United States Patent [19]

Lai et al.

[11] Patent Number: 4,950,671
[45] Date of Patent: Aug. 21, 1990

[54] SUBSTITUTED 2-PROPENYL DERIVATIVES OF PYRIDINE

[75] Inventors: Hoi Kiong Lai, Guelph, Canada; Robert A. Davis, Cheshire, Conn.

[73] Assignees: Uniroyal Chemical Company, Inc., Middlebury, Conn.; Uniroyal Chemical Ltd/Ltee, Don Mills, Canada

[21] Appl. No.: 321,028

[22] Filed: Mar. 9, 1989

[51] Int. Cl.$^5$ .................. A01N 43/40; C07D 211/70; C07D 211/82
[52] U.S. Cl. .................................... 514/277; 546/192; 546/236; 546/348
[58] Field of Search .................. 546/348, 236, 192; 514/277

[56] References Cited

U.S. PATENT DOCUMENTS 4,202,894 5/1980 Pfiffner .............................. 424/248.4

Primary Examiner—Mary C. Lee
Assistant Examiner—Jacqueline Haley
Attorney, Agent, or Firm—Glenn E. Karta

[57] ABSTRACT

A heterocyclic compound having the structural formula

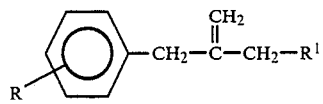

where R is $C_1$-$C_8$ alkyl, $C_3$-$C_6$ cycloalkyl, trifluoromethyl, phenyl, substituted phenyl, phenoxy, substituted phenoxy, benzyl or substituted benzyl; and $R^1$ is at least a partially saturated monocyclic or bicyclic heterocycle of nitrogen which may be substituted with lower alkyl and physiologically acceptable salts thereof is disclosed. A process for forming this compound which involves the reaction of an amine of the formula $HR^1$ where $R^1$ has the meanings given above with a substituted 2-propenyl halide having the structural formula

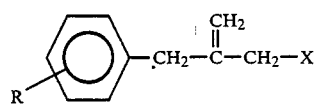

where R has the meanings given above; and X is a halogen atom is described. The invention embodies the above-mentioned novel 2-propenyl halide utilized as an intermediate in the formation of the heterocyclic compound of this invention. A method of controlling phytopathogenic fungi by applying a fungicidally effective amount of the heterocyclic compound of the present invention to the locus under attack by said fungi is also taught. Finally, a fungicidally composition comprising the heterocyclic compound of the present invention and a suitable carrier therefor is set forth.

12 Claims, No Drawings

SUBSTITUTED 2-PROPENYL DERIVATIVES OF PYRIDINE

BACKGROUND OF THE INVENTION

1. Field of the Invention

The present invention is directed to a class of substituted 2-propenyl derivatives of nitrogen heterocycles. More specifically, the present invention is directed to a class of substituted 2-propenyl derivatives of nitrogen heterocycles useful as fungicides.

2. Background of the Prior Art

The control of phytopathogenic fungi is of great economic importance since fungal growth on plants or on parts of plants such as fruits, blossoms, foliage, stems, tubers, roots and the like not only inhibit production of a plant as well as commercially significant portions thereof, its foliage, fruit and seed, but, in addition, reduce the overall quality of the harvested crop.

To overcome or at least reduce the detrimental effects of fungi, plants have long been treated with fungicides. However, the enormous economic toll taken by identified fungi, as well as the development of new fungus strains resistant to known fungicides, establishes a continuing need to develop new and more effective fungicides which possess curative, preventative and systemic action to protect cultivated plants. These new fungicides must not only positively possess these protective properties but, negatively, must not possess properties which have an adverse effect on the plants to be protected.

The use of nitrogen-containing heterocyclic compounds to provide fungicidally effective compositions is known in the art. For example, U.S. Pat. No. 4,202,894 describes a class of heterocyclic compounds, i.e., morpholines, piperidines and the like, which are useful as fungicidal agents. In addition, the compound, 4-(3-(4-(1,1-dimethylethyl)phenyl)-2-methyl)propyl-2,6(cis)-dimethyl-morpholine is dimethyl-morpholine is disclosed in Agricultural Chemicals Book IV - Fungicides, 1985 Revision, W.T. Thomson, Thomson Publications, P.O. Box 9335, Fresno, CA 92341 at page 134. The compound is therein described as a systemic and foliar fungicide. Although the compounds of the above discussed prior art disclosures are nitrogen heterocyclic compounds, they are characterized by a structure which is clearly distinguished from a substituted 2-propenyl derivative of a nitrogen heterocycle.

The above remarks establish the continual need to develop new compounds, distinguished from the compounds utilized in the prior art, that provide more effective fungicidal activity against the scourge of phytopathogenic fungi.

SUMMARY OF THE INVENTION

A new class of substituted 2-propenyl derivatives of nitrogen heterocycles has now been discovered which provides surprisingly effective control of many commonly encountered phytopathogenic fungi. Not only is this new class of compounds effective against many fungi but, in addition, this new class of compounds can be used to control fungi by either systemic or foliar treatment.

In accordance with the present invention, a new class of compounds having the structural formula

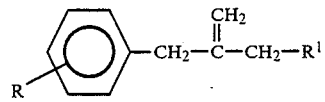

where R is $C_1$-$C_8$ alkyl, $C_3$-$C_6$ cycloalkyl, trifluoromethyl, phenyl, substituted phenyl, phenoxy, substituted phenoxy, benzyl or substituted benzyl: and $R^1$ is an at least partially saturated monocyclic or bicyclic nitrogen-containing heterocycle which may be substituted with lower alkyl and physiologically acceptable salts thereof is disclosed.

In further accordance with the present invention a process for forming the nitrogen heterocyclic compound of the subject invention is described. In this process a unique class of substituted 2-propenyl halides having the structural formula

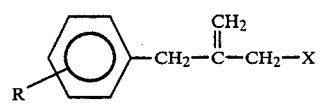

where R is as defined in the compound of the present invention; and X is a halogen atom, is reacted with a compound having the structural formula $HR^1$, where $R^1$ has the meanings given for the compound of the present invention, to form the compound of the subject invention.

In still further accordance with the present invention an intermediate compound, utilized in the formation of the compound of the subject invention, a substituted 2-propenyl halide having the structural formula

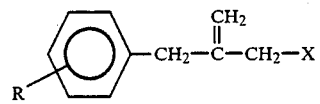

where R is as defined in the nitrogen heterocyclic compound of the present invention; and X is a halogen atom, is set forth.

In yet further accordance with the present invention, a composition comprising the compound of the subject invention and a suitable carrier therefor is taught.

Finally, in yet still further accordance with the subject invention, a method of controlling fungi is disclosed. In this method a fungicidally effective amount of the compound of the present invention is applied to the locus to be protected.

DETAILED DESCRIPTION

The compound of the present invention is a substituted 2-propenyl derivative of a nitrogen heterocycle having the structural formula

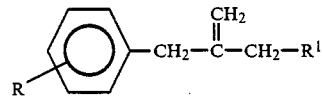

(I)

where R is $C_1$-$C_8$ alkyl, $C_3$-$C_6$ cycloalkyl, trifluoromethyl, phenyl, substituted phenyl, Phenoxy, substituted phenoxy, benzyl or substituted benzyl: and $R^1$ is an at least partially saturated monocyclic or bicyclic nitrogen heterocycle which is linked to 2-propenyl moiety through the nitrogen atom of the heterocycle, and which may contain an oxygen or sulfur atom and which may be substituted with lower alkyl and physiologically acceptable salts thereof.

Preferably, the compound of the present invention has the structural formula I where R is $C_1$-$C_6$ alkyl, $C_5$-$C_6$ cycloalkyl, trifluoromethyl, phenyl, phenoxy or benzyl; and $R^1$ is partially or fully saturated pyrrolyl, pyridyl, isoindolyl, indolyl, isoquinolyl, quinolyl, morpholinyl, thiomorpholinyl or azepinyl which may be substituted with $C_1$-$C_2$ alkyl and physiologically acceptable salts thereof.

More preferably, the compound of the present invention is a compound having the structural formula I where R is tert-butyl, cyclohexyl, trifluoromethyl, phenyl or phenoxy: and $R^1$ is at least partially saturated pyridyl, morpholinyl, indolyl, quinolyl or isoquinolyl which may be substituted with one or more methyl groups and physiological acceptable salts thereof.

In a preferred embodiment of the compound of the instant invention, the compound having the structural formula I, the substituent R is positioned para to the substituted propenyl group on the phenyl ring.

In the preferred embodiment wherein the nitrogen heterocyclic group of $R^1$ is substituted with lower alkyl groups, the number of such alkyl substituents is preferably 1 or 2. Moreover, in the preferred embodiment wherein a physiological acceptable salt of the compound having the structural formula I is utilized, it is preferably a hydrochloride salt.

The subject invention is also directed to an intermediate compound, a substituted 2-propenyl halide having the structural formula

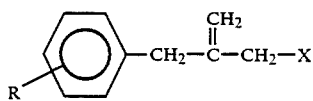

(II)

where R has the meanings given for the broadest meaning of the compound having the structural formula I; and X is a halogen atom.

Preferably, the intermediate compound having the structural formula II is defined by R having the meanings of the preferred embodiment of the compound having the structural formula I; and X is chlorine or bromine.

More preferably, the compound having the structural formula II is defined by R having the meanings of the more preferred embodiment of the compound having the structural formula I; and X is chlorine.

In an another aspect of the present invention, a process is provided for making the compound having the structural formula I. In that process a Grignard reagent having the structural formula

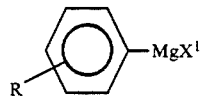

(III)

where R has the meanings given for the compound having the structural formula I; and $X^1$ is a halogen atom, is reacted with a methallyl halide having the structural formula

where X is halogen. Preferably, the compound having the structural formula IV is characterized by X being chlorine or bromine. More preferably, X is chlorine.

The reaction of the Grignard reagent, the compound characterized by the structural formula III, and the methallyl halide, having the structural formula IV, are reacted in a solvent, preferably, diethyl ether or tetrahydrofuran.

The product of this reaction is the intermediate compound of the present invention, the substituted 2-propenyl halide defined by structural formula II. This intermediate compound is reacted with a compound of the formula $$HR^1 \quad (V)$$

wherein $R^1$ has the same meanings as that given to the broadest meaning of $R^1$ in the definition of the compound having the structural formula I.

The reaction between the substituted propenyl halide, having the structural formula 11, and the amine, having the structural formula V, occurs at a temperature in the range of between about 80° C. and 130° C. The reaction can occur in the presence or absence of a solvent. If a solvent is employed, the reactants, the compounds having the structural formulas II and V, are heated to the reflux temperature of the solvent.

In the preferred embodiment wherein a solvent is employed it is an inert hydrocarbon or an inert chlorohydrocarbon of sufficiently high boiling point to meet the temperature constraint mentioned above. Thus, solvents preferred for use in this application include toluene, xylene and dichlorobenzenes.

The preferred stoichiometric ratio of the reactants which result in the formation of the desired compound having the structural formula I is two molar equivalents of the amine having the structural formula V to one molar equivalent of the intermediate compound having the structural formula II.

For completeness, it should be mentioned that the formation of the compound having the structural formula I includes the step of neutralizing the crude product obtained by the reaction of compounds having the structural formula II and V with a base prior to the isolation of the product, the compound having the structural formula I.

In addition to the compound having the structural formula I, the instant invention encompasses physiologically acceptable salts thereof. These salts are obtainable by dissolving a compound having the structural formula I, synthesized by the above-defined procedure, in a suitable inert solvent and adding an acid thereto. The reaction product is isolated and purified. For example, the product may be filtered and, if necessary, purified by washing with an inert organic solvent. The preferred acid utilized in the salt formation process is hydrochloric acid, resulting in the formation of the preferred salt, the hydrochloride salt of the compound having the structural formula I. Other acids which may be used in forming a salt within the contemplation of the present invention include nitric acid and sulfuric acid.

In the preferred embodiment wherein the compound of the present invention, having the structural formula I, is characterized by a substituted nitrogen heterocyclic, that compound is obtained by employing an amine, having the structural formula V, wherein one or more of the ring carbon atoms are substituted with lower alkyl, preferably methyl.

It should be appreciated that in the case where $R^1$ has a meaning wherein the heterocyclic nitrogen ring is substituted with two lower alkyl groups that compound may be present as a pair of cis and trans isomers. These isomers may or may not be separated. Thus, the compound of the present invention, wherein the nitrogen heterocyclic ring is substituted with two lower alkyl groups, contemplates mixtures of cis and trans isomers.

It is also emphasized that in the case where the compound having the structural formula I is characterized by lower alkyl substitution on the heterocyclic nitrogen ring, that substitution is preferably $C_1$–$C_2$ alkyl. More preferably, the substituent is methyl. It is particularly preferred, in the case of heterocycle substitution, that the substituent be one or two methyl groups.

Yet another aspect of the present invention is a method for controlling phytopathogenic fungi. In this method a fungicidally effective amount of the compound having the structural formula I, where the meanings of R and $R^1$ are those given for the broadest meaning of the compound of that formula, is applied to the locus under attack by said fungi. Preferably, the method of controlling phytopathogenic fungi comprises applying a fungicidally effective amount of a compound having the structural formula I, where R and $R^1$ have the meanings of the preferred embodiment of that compound, to the locus under attack by said fungi. More preferably, the method of controlling phytopathogenic fungi comprises applying a fungicidally effective amount of a compound having the structural formula I, where R and $R^1$ have the meanings given for the more preferred embodiment of the compound having the structural formula I, to the locus under attack by said fungi.

In one preferred embodiment, the method by which a fungicidally effective amount of the compound having the structural formula I is applied to the locus under attack by said phytopathogenic fungi is by application of the compound having the structural formula I to the foliage of the plants to be protected. This so-called "foliar treatment" is effectuated by applying the compound having the structural formula I to the foliage at a concentration of between about 10 and about 500 milligrams of the compound having the structural formula I per liter of inert liquid in which the compound is disposed to the foliage of the plants to be protected from the phytopathogenic fungi.

In another preferred embodiment of the method of controlling phytopathogenic fungi, a fungicidally effective amount of the compound having the structural formula I is applied to the soil in which the plants to be protected from the fungi are grown. In this method, the so-called "systemic treatment," a compound having the structural formula I is applied to the soil in which the plant to be protected is grown in a concentration of between about 0.125 and about 10 kilograms of the compound having the structural formula I per hectare (kg/ha) of soil in which the plant to be protected is grown. More preferably, systemic control involves application of between about 0.125 kg/ha to about 5 kg/ha of the compound having the structural formula I to the soil in which the plant to be protected is grown.

Independent of which preferred embodiment of controlling fungi is utilized, either the foliar or systemic treatment, the application may be applied prior to or after infection by fungi. Furthermore, it should be appreciated that the exact dosage, applied systemically or to the foliage, is dictated by the fungus to be controlled and the particular plant to be protected.

In still another embodiment of the method of the present invention of controlling phytopathogenic fungi, the compound having the structural formula I is applied as a coating to the seeds of the plant to be protected. This method benefits from the two preferred embodiments discussed above, foliar treatment and systemic treatment. That is, the fungicidal coating, the coating of the compound having the structural formula I, protects the soil from infection by the fungi and is also taken up by the plant systemically to protect the plant from fungal attack. In this so-called "seed coating method," an appropriate concentration of the compound having the structural formula I is in the range of between about 5 and about 75 grams of the compound per hundred kilograms of seed.

Another important aspect of the present invention resides in a new composition useful as a fungicide. The fungicidal composition of the present invention comprises a compound having the structural formula I, where R and $R^1$ have the meanings given for the broadest meaning of that compound, and a carrier therefor.

Preferably, the composition of the instant invention includes a compound having the structural formula I, where R and $R^1$ have the meanings given for the preferred embodiment of that compound, and a carrier therefor.

More preferably, the fungicidal composition of the present invention includes a compound having the structural formula I, where R and $R^1$ have the meanings given for the more preferred embodiment of the compound having the structural formula I, and a carrier therefor.

The utility of the composition, as stated above, is as a fungicide. Therefore, in a preferred embodiment, the concentration of the component of the composition defined by the compound having the structural formula I is a fungicidally effective amount of that compound. This concentration applies to the broadest, preferred and more preferred embodiments of the composition of this invention.

The composition of the present invention includes, as one component thereof, a carrier suitable for admixture with the active agent of the composition, a compound having the structural formula I. The identity of the carrier is very broad. The carrier may be a solid, for example, finely divided particulate solids, granules, pellets, wettable powders, soluble powders and the like. Among the solid carriers within the contemplation of the subject invention are such organic and inorganic materials as attapulgite clay, sand, vermiculite, corncob, activated carbon and mineral silicates. Among the mineral silicates preferred for use in the composition of the present invention are mica, talc, pyrophyllite, clays and the like.

A solid composition may be prepared from a solid carrier, such as one of those described immediately above. In that case, the active compound is impregnated onto the solid carrier. Alternatively, the active compound may be formulated into a wettable powder by grinding it into a fine powder and mixing it with the solid carrier to which a surface active dispersing agent has been added. The wettable powder is then dispersed in water and applied as a dispersion.

Indeed, the above described dispersion is representative of a composition which may also be classified as a liquid composition. In addition to liquid dispersions, the liquid composition may be in the form of a solution or an emulsion. In the case of a liquid solution, the active compound, the compound having the structural formula I, is dissolved in an aqueous or organic solvent. In most cases the solvent, which acts as the carrier, is organic. In addition to aromatic hydrocarbons, such as toluene and xylene, other preferred solvents include such organic compounds as acetone, methanol, isopropanol, t-butyl alcohol, cyclohexanone, dioxane, dimethylformamide, dimethyl sulfoxide, ethylene dichloride, diacetone alcohol and N-methylpyrrolidone.

A water emulsion, another preferred embodiment of a liquid composition within the contemplation of the present invention, is prepared from a solution, as described above, to which a surface active agent is added. Surface active agents suitable for use in forming an emulsion within the contemplation of this invention are known to those skilled in the art. *McCutcheon's Detergents and Emulsifiers*, Allured Publishing Corp., Ridgewood, N.J. (1970): U.S. Pat. No. 2,514,916, at Columns 2 to 4; and U.S. Pat. No. 2,547,734, at Columns 3 and 4, provide detailed examples of such surface active agents suitable for this purpose. As indicated in these references, the surface active agent may be anionic, non-ionic or cationic.

In yet another embodiment of the carrier component of the composition of this invention, the carrier is an aerosol. To prepare an aerosol, the active compound, the compound having the structural formula I, is dissolved in a first solvent. This first solvent is conventional in the sense that although it is volatile, it is not highly volatile. This solution is then admixed with a highly volatile solvent, a so-called liquid aerosol carrier. The aerosol carrier is liquid only under elevated pressure. At ambient temperature and pressure, the aerosol carrier is a gas. In a subembodiment of this preferred carrier, the aerosol carrier may itself be active. For example, the carrier may be an insecticide, a herbicide, a bacteriacide or the like.

The following examples are given to illustrate the present invention. Because these examples are given for illustrative purposes only, these examples should not be interpreted as limiting the invention to the scope of the examples recited hereinafter.

EXAMPLE 1

Preparation of 2-[(P-t-butylphenyl)methyl]-2-propenyl Chloride

A solution of p-bromo-(t-butyl)benzene (21.3 g., 0.10 mole) in dry diethyl ether (100 ml.) was added dropwise to a mixture of magnesium turnings (2.4 g.), a single iodine crystal and dry diethyl ether (50 ml.). The mixture was allowed to react at ambient temperature for two hours. The resultant Grignard solution was transferred to a dry dropping funnel and added dropwise to a solution of methallyl dichloride (13 8 g., 0.11 mole) in dry diethyl ether (50 ml.). After complete addition of the Grignard solution, the mixture was refluxed for three hours and thereafter cooled with an ice-water bath while 15% hydrochloric acid (150 ml.) was added thereto. The mixture was extracted with diethyl ether and the organic phase dried over sodium sulfate, filtered and evaporated to yield a liquid. The liquid was distilled to provide 10 grams of 2-[(p-t-butylphenyl)methyl]-2-propenyl chloride. This product was characterized by a boiling point of 105° C. to 111° C. at a pressure of 0.25 mm Hg.

EXAMPLE 2

Preparation of 4-[2-[(P-t-butylphenyl)methyl]-2-propenyl]-2,6-dimethylmorpholine (Compound No. 1)

A mixture of 2-[(p-t-butylphenyl)methyl]-2-propenyl chloride (7.4 g., 0.033 mole), formed in accordance with the procedure of Example 1, and 2,6-dimethylmorpholine (7.7 g., 0.067 mole) was heated for five hours at 120° C. The thus heated mixture was cooled to room temperature and then treated with 25% aqueous sodium hydroxide (20 ml.). The mixture was extracted with toluene, dried over sodium sulfate and evaporated to give an oil. The oil was distilled to yield 7.0 grams of 4-[2-[(p-t-butylphenyl)methyl]-2-propenyl]-2-6-dimethylmorpholine. The product was characterized by a boiling point of 143° C.–147° C. at 0.25 mm Hg.

EXAMPLE 3

Preparation of 1-[2-[[(P-trifluoromethyl)phenyl]methyl]-2-propenyl]-3,5-dimethylpiperidine (Compound No. 29)

In a method analogous to that described in Example 2, 2-(p-trifluoromethyl)benzyl-2-propenyl chloride (5.0 g., 0.021 mole), formed in a method analogous to that utilized in Example 1, was reacted with 3,5-dimethylpiperidine (4.8 g., 0.042 mole) at 120° C. for six hours to produce, after extraction, drying, evaporation and distillation, 4.5 grams of 1-[2-[[(p-trifluoromethyl)phenyl]methyl]-2-propenyl]-3,5-dimethylpiperidine. The formed compound was characterized by a boiling point of 80° C. to 85° C. at 0.25 mm Hg.

EXAMPLE 4

Preparation of 1-[2-[[(P-trifluoromethyl)phenyl]methyl]-2-propenyl]-3,5-dimethylpiperidine, hydrochloride (Compound No. 31)

A solution of 2-[[(p-trifluoromethyl)phenyl]-methyl]-2-propenyl]-3,5-dimethylpiperidine (2.0 g.), made in accordance with Example 3, in diethyl ether (50 ml.) was treated with a steady stream of hydrogen chloride gas until white solid precipitation ceased. The precipitated solid was collected by filtration and air dried to give 1.5 grams of 1-[2-[[(p-trifluoromethyl)phenyl]methyl]-2-propenyl]-3,5-dimethylpiperidine, hydrochloride. This salt product was characterized by a melting point of 150° C. to 151° C.

EXAMPLE 5

Preparation of 1-[2-[(P-t-butylphenyl)methyl]-2-propenyl]-decahydroquinoline (Compound No. 8)

2-[(P-t-butylphenyl)methyl]-2-propenyl chloride (2.3 g., 0.010 mole), formed in accordance with the procedure of Example 1, was reacted with perhydroisoquinoline line (3.0 g., 0.022 mole) at 120° C. for five hours. The product of this reaction was separated and purified by the steps employed in Example 2 to yield 2.8 grams of 1-[2-](p-t-butylphenyl)-methyl]-Z-propenyl]-decahydroquinoline which was identified by its boiling point, 157° C. at 0.025 mm Hg.

EXAMPLE 6

Preparation of 1-[2-[(P-t-butylphenyl)methyl]-2-propenyl]-2,3-dihydro-(1H)-indole (Compound No. 23)

2-[(P-t-butylphenyl)methyl]-2-propenyl chloride (4.5 g., 0.020 mole), formed in accordance with the procedure of Example 1, was reacted with indoline (4.8 g., 0.040 mole) at 120° C. for five hours and processed in accordance with the procedure of Example 2 to provide 2.6 grams of 1-[2-[(p-t-butylphenyl)methyl]-2-propenyl]-2,3-dihydro-(1H)-indole which was identified by its boiling point, 138° C. to 145° C. at 0.02 mm Hg.

EXAMPLE 7

Preparation of 1-[2-[(P-phenoxyphenyl)methyl]-2-propenyl]-3-methylpiperidine (Compound No. 11)

2-[(P-phenoxyphenyl)methyl]-2-propenyl chloride (5.0 g., 0.020 mole), formed in a method analogous to that utilized in Example 1, was reacted with 3-methylpiperidine (3.8 g., 0.038 mole) at 110° C. for five hours. The product was processed in accordance with the procedure of Example 2 to yield 4.0 grams of 1-[2-[(p-phenoxyphenyl)methyl]-2-propenyl]-3-methylpiperidine. The thus formed compound was characterized by a boiling point of 175° C. to 183° C. at 0.1 mm Hg.

EXAMPLE 8

Preparation of 1-[2 [(4-Phenyl)benzyl]-2-propenyl]-4-methylpiperidine (Compound No. 33)

A mixture of 2-[(4-phenyl)benzyl]-2-propenyl chloride (4 g.), formed in a manner analogous to that used in Example 1, and 4-methylpiperidine (3.3 g.) in p-xylene (15 ml.) was refluxed for five hours, cooled and neutralized with 25% aqueous sodium hydroxide (15 ml.). The mixture was extracted with toluene, dried over sodium sulfate and evaporated under reduced pressure to give an oil. The oil was distilled under vacuum and the fraction boiling at 195° C. to 200° C. at a pressure of 0.7 mm Hg. was collected and identified as 1-[2-[(4-phenyl)benzyl]-2-propenyl]-4-methylpiperidine. The compound, obtained in a yield of 3.5 g., solidified after being left at room temperature for a few hours. The solid was characterized by a melting point of 53° C.

EXAMPLE 9

Preparation of 1-[2-[(4-Phenyl)benzyl]-2-propenyl]-3,5-dimethylpiperidine (Compound No.34)

A mixture of 2-[(4-phenyl)benzyl]-2-propenyl chloride (4 g.), synthesized by method utilized in Example 1, and 3,5-dimethylpiperidine (3.7 g.) was heated at 120° C. for five hours. The mixture was cooled to room temperature and neutralized with 25% aqueous sodium hydroxide (15 ml.). The mixture was extracted with toluene, dried over sodium sulfate and evaporated to give an oil which partially solidified on standing. The product was triturated with petroleum ether, having a boiling point range of 30° C. to 60° C., and the insoluble material was removed by filtration. The filtrate was evaporated under reduced pressure to yield 1-[2-[(4-phenyl)benzyl]-2-propenyl]-3,5-dimethylpiperidine in a yield of 4.9 grams.

The compound was identified by its nuclear magnetic resonance data which was as follows: NMR (CDCl$_3$) δ: 7.1–7.6(9H,m), 4.95(1H,s), 4.85(1H,s), 3.4(2H,s), 2.8(2H,s), 1.2–2.5(8H,m), 0.95(3H,d), 0.8(3H,d).

EXAMPLE 10

Preparation of Compound Nos. 2–7, 9, 10, 12–22, 24–28, 30, 32 and 35–49

Additional compounds characterized by structural formula I, wherein R and R$^1$ have meanings within the contemplation of the present invention, were prepared in accordance with the procedures enurerated in Examples 1 to 9. These compounds, including their characterizing boiling points, melting points or NMR data are summarized in Table I, which appears below. For convenience, the equivalent data for Compound Nos. 1, 8, 11, 23, 29, 31, 33 and 34, formed in accordance with Examples 2 to 9, respectively, are also included in Table I.

TABLE 1

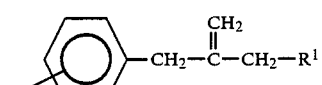

| Cpd. No. | R | R$^1$ | B.P. (°C.)/mm Hg | NMR or M.P. (°C.) |
|---|---|---|---|---|
| 1 | 4-C(CH$_3$)$_3$ | 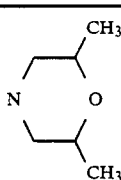 | 143–147/0.25 | |
| 2 | 4-C(CH$_3$)$_3$ | (piperidine) | 170/1.80 | |

TABLE 1-continued

Structure: R-C₆H₄-CH₂-C(=CH₂)-CH₂-R¹

| Cpd. No. | R | R¹ | B.P. (°C.)/mm Hg | NMR or M.P. (°C.) |
|---|---|---|---|---|
| 3 | 4-C(CH₃)₃ | 2,6-dimethylpiperidin-1-yl | 124/0.025 | |
| 4 | 4-C(CH₃)₃ | 4-methylpiperidin-1-yl | 135/0.20 | |
| 5 | 4-C(CH₃)₃ | 3-methylpiperidin-1-yl | 178–180/1.30 | |
| 6 | 4-C(CH₃)₃ | 2-methylpiperidin-1-yl | 115/0.10 | |
| 7 | 4-C(CH₃)₃ | 3,5-dimethylpiperidin-1-yl | 120–124/0.10 | |
| 8 | 4-C(CH₃)₃ | decahydroisoquinolin-2-yl | 157/0.025 | |
| 9 | 4-C₆H₅ | 2,6-dimethylmorpholin-4-yl | 175–180/0.05 | |
| 10 | 4-C₆H₅O | 2,6-dimethylmorpholin-4-yl | 175–180/0.05 | |
| 11 | 4-C₆H₅O | 3-methylpiperidin-1-yl | 175–183/0.10 | |

TABLE 1-continued

Structure: phenyl ring with R substituent, connected to -CH₂-C(=CH₂)-CH₂-R¹

| Cpd. No. | R | R¹ | B.P. (°C.)/mm Hg | NMR or M.P. (°C.) |
|---|---|---|---|---|
| 12 | 4-C₆H₅O | piperidin-1-yl | 165–175/0.10 | |
| 13 | 3-CF₃ | 2,6-dimethylmorpholin-4-yl | 88–90/0.10 | |
| 14 | 3-CF₃ | 3-methylpiperidin-1-yl | 75–78/0.10 | |
| 15 | 3-CF₃ | 2,6-dimethylpiperidin-1-yl | 114–116/0.60 | |
| 16 | 3-CF₃ | piperidin-1-yl | 95–97/0.50 | |
| 17 | 3-CF₃ | 3,5-dimethylpiperidin-1-yl | 110–112/0.50 | |
| 18 | 3-CF₃ | 2,6-dimethylmorpholin-4-yl · HCl | | 162–164 |
| 19 | 3-CF₃ | 3-methylpiperidin-1-yl · HCl | | 144–146 |
| 20 | 3-CF₃ | 3,5-dimethylpiperidin-1-yl · HCl | | 135–138 |

TABLE 1-continued $$\text{R}-\underset{}{\text{C}_6\text{H}_4}-\text{CH}_2-\underset{\|\text{CH}_2}{\text{C}}-\text{CH}_2-\text{R}^1$$

| Cpd. No. | R | R¹ | B.P. (°C.)/mm Hg | NMR or M.P. (°C.) |
|---|---|---|---|---|
| 21 | 3-CF₃ | 2-methylpiperidine·HCl | | * |
| 22 | 4-cyclohexyl | 2,6-dimethylmorpholine | 180–185/0.05 | |
| 23 | 4-C(CH₃)₃ | indoline | 138–145/0.02 | |
| 24 | 4-C(CH₃)₃ | 1,2,3,4-tetrahydroisoquinoline | 140–145/0.025 | |
| 25 | 4-C(CH₃)₃ | 1,2,3,4-tetrahydroisoquinoline | 140/0.025 | |
| 26 | 4-C(CH₃)₃ | indoline·HCl | | ** |
| 27 | 4-C(CH₃)₃ | octahydroindole | 134–136/0.02 | |
| 28 | 4-CF₃ | 2,6-dimethylmorpholine | 90–95/0.025 | |
| 29 | 4-CF₃ | 3,5-dimethylpiperidine | 80–85/0.025 | |
| 30 | 4-CF₃ | 3-methylpiperidine | 100–105/0.70 | |

TABLE 1-continued

Structure: aryl–CH₂–C(=CH₂)–CH₂–R¹ with R on the phenyl ring

| Cpd. No. | R | R¹ | B.P. (°C.)/mm Hg | NMR or M.P. (°C.) |
|---|---|---|---|---|
| 31 | 4-CF₃ | 3,5-dimethylpiperidine·HCl | | 150–151 |
| 32 | 4-CF₃ | 3-methylpiperidine·HCl | | 161–163 |
| 33 | 4-C₆H₅ | 4-methylpiperidine | 195–200/0.70 | 53 |
| 34 | 4-C₆H₅ | 3,5-dimethylpiperidine | | *** |
| 35 | 4-C₆H₅ | 2,6-dimethylpiperidine | 192–196/0.25 | |
| 36 | 4-C₆H₅ | 3-methylpiperidine·HCl | | 161–163 |
| 37 | 4-C₆H₅ | piperidine | 176–183/0.25 | |
| 38 | 4-C₆H₅ | decahydroisoquinoline | | **** |
| 39 | 4-C₆H₅ | piperidine·HCl | | 200–201 |
| 40 | 4-C₆H₅ | 3-methylpiperidine | 185–193/0.25 | |

TABLE 1-continued
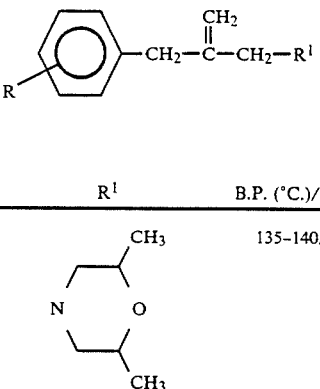
| Cpd. No. | R | R¹ | B.P. (°C.)/mm Hg | NMR or M.P. (°C.) |
|---|---|---|---|---|
| 41 | 4-CH₃ | 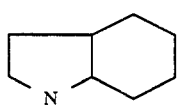 | 135-140/5.00 | |
| 42 | 4-C₆H₅O | 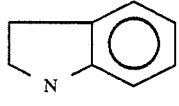 | 192-198/0.05 | |
| 43 | 4-C₆H₅O | 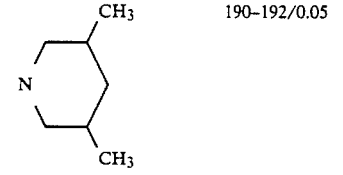 | | 190-198/0.05 |
| 44 | 4-C₆H₅O | 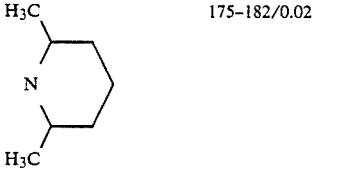 | 190-192/0.05 | |
| 45 | 4-C₆H₅O | 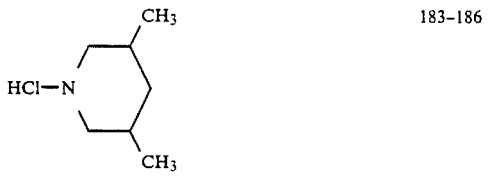 | 175-182/0.02 | |
| 46 | 4-C₆H₅ | 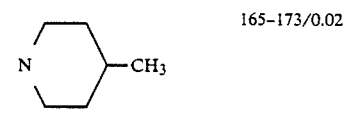 | | 183-186 |
| 47 | 4-C₆H₅O | 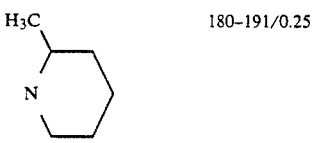 | 165-173/0.02 | |
| 48 | 4-C₆H₅O |  | 180-191/0.25 | |

TABLE 1-continued $$R-\text{C}_6\text{H}_4-\text{CH}_2-\overset{\overset{\displaystyle \text{CH}_2}{\|}}{\text{C}}-\text{CH}_2-R^1$$

| Cpd. No. | R | R¹ | B.P. (°C.)/mm Hg | NMR or M.P. (°C.) |
|---|---|---|---|---|
| 49 | 4-C₆H₅O | (pyrrolidin-1-yl) | 165–173/0.05 | |

*NMR (CDCl₃) δ: 9.5(1H, broad), 7.1–7.5(8H, m), 5.45(1H, s), 5.35(1H, s), 3.9(2H, s), 3.5(2H, s), 3.2(4H, m), 1.3(9H, s)
**NMR (CDCl₃) δ: 11.5(1H, broad), 7.2–7.6(4H, m), 5.5(1H, s), 5.3(1H, s), 3.8(2H, s), 3.6(2H, s), 3.3(2H, m), 1.6(6H, m), 1.4(3H, t), 1.2(2H, t)
***NMR (CDCl₃) δ: 7.1–7.6(9H, m), 4.95(1H, s), 4.85(1H, s), 3.4(2H, s), 2.8(2H, s), 1.2–2.5(8H, m), 0.95(3H, d), 0.8(3H, d)
****NMR (CDCl₃) δ: 7.1–7.8(9H, m), 5.0(1H, s), 4.9(1H, s), 3.5(2H, s), 3.0(2H, s), 2.5–2.9(4H, m), 0.9–2.1(12H, m)

EXAMPLE 11
Preparation of Fungicidal Compositions

Compound Nos 1 to 49, summarized in Table I above, were each dissolved in acetone or other suitable solvent (0.3 g. of each of the compounds in 10 ml. of acetone or other suitable solvent). One or two drops of an emulsifying agent, Triton [trademark]X-100, and water were added to the solution to form an emulsion. The amount of water added was a function of the desired concentration of the emulsion composition, reported in milligrams per liter (mg/1).

EXAMPLE 12
Control of Powdery Mildew Fungus by Systemic Root Uptake

Compositions of Compound Nos. 1 to 49, formed in accordance with the procedure of Example 11, were tested to evaluate their effectiveness in preventing or controlling powdery mildew disease of barley caused by the fungus, *Erysiphe graminis* and powdery mildew disease of cucumber caused by the fungus, *Erysiphe cichoracearum*. This prevention or control capability was tested by utilizing the compounds of the present invention to control these diseases by systemic root uptake.

In accordance with this aim, pots (4×4×3.5 inches) containing 10 plants of barley (Variety "Herta") or 10 plants of cucumber (Variety "Marketmore 70") were grown to an age of six days and ten days, respectively. Upon reaching these ages, emulsion compositions (45 ml.) of Compounds 1 to 49, formed in accordance with the procedure of Example 11, were added to each pot. That is, 45 ml. an emulsion composition of each of the compounds tabulated in Table I were separately added to pots containing 10 barley or 10 cucumber plants of the type enumerated above. The 45 ml. of each of the emulsion compositions were added to each of the pots and saturated the soil in each pot without significant loss through drainage into the saucers below the pots. Each of the compositions contained the compounds of the present invention in a concentration of 250 milligrams of the compound per liter of water (mg/1). A number of pots containing the same barley and cucumber plants were left untreated as controls.

The barley and cucumber plants in all the pots, including those treated and those untreated, were inoculated with powdery mildew fungus 24 hours after emulsion composition treatment with the compounds of the present invention. Fungus inoculation was accomplished by tapping leaves of previously infected barley and cucumber plants over the treated and untreated pots containing the barley and cucumber plants, respectively, to distribute spores of the fungus over the plants growing in the pots.

Six days after inoculation, disease control was evaluated on a 0 to 6 rating scale. A 0 rating was assigned when no disease was evidenced. A 6 rating was given for severe disease. Intermediate ratings were assigned depending on the degree of disease. Percent control was computed by comparing the ratings of the treated and untreated plants.

The results of this test are reported in Table II wherein systemic control of powdery mildew disease in barley is reported under the title "BMS 250." Control of cucumber powdery mildew disease is reported, in Table II, under the title "CMS 250."

EXAMPLE 13
Control of Powdery Mildew Fungus by Foliar Application

Eight plants of barley (Variety "Larker") were planted in a pot. The number of pots, as in Example 12, were sufficient to accommodate testing in duplicate or triplicate for each of the 49 compounds tabulated in Table I. This number included a duplicate number of pots, each containing eight plants, which acted as controls.

In this test each of the compounds formulated into emulsion compositions, at a concentration of 1,000 milligrams of the compound per liter of water (1,000 mg/1), were prepared. These emulsions were then sprayed onto the foliage of the barley plants. The pots in which the plants were unsprayed acted as controls. The number of pots which were unsprayed equalled the number sprayed.

After the foliage of the sprayed pots were dried the pots containing the sprayed and the unsprayed plants were all placed in a greenhouse maintained at 21° C. All the plants in the pots were thereupon inoculated with barley powdery mildew fungus, *Erysiphe graminis*. Inoculation of the fungus was again accomplished by distributing spores of the fungus over the leaves of the plants to be tested from plants which had previously been infected with the disease.

Five days after inoculation, the plants were evaluated and assigned a disease rating of 0 to 6 in accordance with the criterion explained in Example 12. Percentage control was computed in accordance with the description of Example 12. The results of these tests are summarized in Table II under the title "BMP 1,000."

Similarly, pinto bean plants were prepared, treated and innoculated with *Erysiphe Polygoni* (PMP) as described above and reported in Table II.

EXAMPLE 14

Control of Rice Blast Disease by Foliar Treatment

Five rice plants (Variety "Bellemont") were grown in a plurality of pots. The number of pots utilized equalled two times the number of compounds of the present invention in Table I plus a control for each replication of the test.

The non-control pots were sprayed with emulsion compositions, formed in accordance with the procedure of Example 11, wherein each compound was provided in a concentration of 1,000 mg/l. This spraying occurred 3 to 4 weeks after planting of the plants in the pots. The controls remained unsprayed.

The sprayed and unsprayed plants, five to a pot, were inoculated with spores of the rice blast fungus, *Pyricularia oryzae*. This inoculation was accomplished by preparing inoculum containing 20,000 to 30,000 spores per milliliter. The inoculum was sprayed onto the plants to which one or two drops of ethoxylated sorbitan monolaurate surfactant had been earlier applied to ensure proper wetting of the inoculum onto the plant foliage.

The inoculated plants in the control and non-control pots were incubated in a control chamber, at a humidity of 99% and a temperature of 21° C., for about 24 hours to allow infection to occur. The plants, after 24 hours in the control chamber, were transferred to a greenhouse for six days to permit disease development to occur. Disease was manifested by blast lesions on the leaves. Disease control was calculated by one of two methods. In one method the number of lesions were counted, if infection was moderate. Alternatively, in the case of severe infection, disease was evaluated by the 0 to 6 rating system discussed in Example 12. Whichever disease control rating system was employed to determine disease control of any particular compound was also utilized in evaluating its control.

The results of this test are tabulated in Table II under the title of "RCB 1,000."

EXAMPLE 15

Control of Bean Rust Fungus Eradicant Test

Two pinto bean plants, *P. vulgaris*, were planted in a plurality of pots. When the plants were seven days old, at the primary leaf stage of growth, they were all sprayed with a suspension containing 20,000 spores of the bean rust fungus, *Uromyces phaseoli*, per milliliter of suspending water. All the pots containing the inoculated plants were then incubated in a controlled environmental chamber, maintained at 99% humidity and 21° C., for 24 hours to allow infection to develop. The plants were then removed from the incubator and allowed to dry. Two days after inoculation the infected plants were sprayed with compositions of the compounds tabulated in Table I. The compositions were prepared in accordance with the procedure of Example 11 to provide a dosage of 1,000 mg/l. An equal number of infected plants were not sprayed so that they could act as controls. All the sprayed and unsprayed plants were placed in a greenhouse, maintained at a temperature of 21° C., for five days to allow any disease present to be expressed.

The sprayed and control plants were assessed for disease using the 0 to 6 rating system described in Example 12. Disease control, as discussed in Example 12, was then determined. The control of disease, expressed as percent reduction of disease, is included in Table II under the title "BRE 1,000."

EXAMPLE 16

Control of Peanut Cercospora Leafspot by Foliar Treatment

Four Virginia peanut plants were grown in each of a plurality of pots. Enough pots were prepared so that each of the compounds listed in Table I, prepared as emulsion compositions in accordance with the procedure of Example 11, could be evaluated by spraying each of them on the four plants of one pot. An equal number of pots, which were not sprayed, were provided as controls. Spraying occurred when the plants were four weeks old. The concentration of the emulsion utilized to spray the peanut plants was 900 mg/l.

All the plants, both sprayed and unsprayed (the controls), were thereafter inoculated with spores of Peanut Cercospora leafspot, *Cercospora arachidicola*. The inoculum contained 20,000 to 30,000 spores per milliliter. The inoculum (which had been previously treated with one or two drops of ethoxylated sorbitan monolaurate to aid in wetting the leaves) was sprayed onto the leaves of the peanut plants. All the pots containing the inoculated peanut plants were incubated in a control chamber, maintained at 24° C., for 36 hours to develop infection. The plants were then placed in a greenhouse for 21 days to allow disease development.

After 21 days in the greenhouse, all the plants were taken out and evaluated using the 0 to 6 disease rating system. Percent control was computed and the results are reported in Table II under the title "PNT 900."

EXAMPLE 17

Control of Barley Blast by Foliar Treatment

A plurality of pots which included 10 plants of 6 day old barley (Variety "Herta") were prepared. These pots were sprayed with emulsion compositions, formulated in accordance with the procedure of Example 11, of each of the compounds set forth in Table I.

The plants in these pots, plus an equal number of 6 day old Variety "Herta" barley plants in control pots, which were unsprayed, were inoculated with spores of the blast fungus, *Pyricularia oryzae*. The method of inoculation utilized was the same as that enumerated in Example 14, which employed the same fungus.

All the inoculated plants were placed in a greenhouse, maintained at a temperature of 21° C. and a humidity of 99%, for five days. At that time, the plants were evaluated using the 0 to 6 disease rating system. Percent control was computed and the results of this test are included in Table II under the title "BBL 1,000."

EXAMPLE 18

Control of Eight Fungus Species

Each of the compounds, Compound Nos. 1 to 49, listed in Table I were solubilized in acetone at a concentration of 500 mg/l. Filtered paper discs, each 11 mm.

in diameter, were dipped in each of the test solutions. The discs were allowed to dry in air to drive off the acetone solvent. An equal number of discs were untreated and acted as controls.

Each of the treated and untreated discs were then placed on agar plates and seven fungus species: *Alternaria solani* (ALT), *Botrytis cinerea* (BOT), *Fusarium oxysporum* (FUS), *Helminthosporium maydis* (HMAY), *Phytophthora infestans* (PHY), *Sclerotinia sclerotiorum* (SCM) and *Sclerotium rolfsii* (SCO) were added to the center of each disc in the form of a culture plug with the fungus mat in contact with the treated paper of the test disc or, in the case of the controls, in contact with the untreated test paper. The plates were incubated at 29° C. in an oven.

Percent growth inhibition by the compounds of the present invention of the seven fungus species was evaluated, after incubation, by measuring the radius from the center of the fungus colony of the treated discs compared to the radius from the center of the fungus colony of the untreated discs. That is, inhibition effectuated by each of the compounds was determined as a function of the percent difference between the radii of the treated and untreated discs. The results of these tests appear in Table II under the titles "ALT 500," "BOT 500," "FUS 500," "HMAY 500," "PHY 500," "SCM 500," and "SCO 500."

It is noted that in the case of the test of the fungus *Helminthosporium maydis*, the concentration of each of Compound Nos. 1 to 49 was 500 milligrams per liter.

A separate test was utilized to determine the control of a eighth fungi species, *Cercospora arachidicola* (CER). In this test two drops of the fungus were added as a spore suspension (20,000 spores per milliliter) to the chemically treated discs, rather than as a mycelial culture plug. Scoring of the effectiveness of the compounds in controlling the *Cercospora arachidicola* fungus was determined with control based on the following scoring criteria: 100 represented complete inhibition of germination and growth of the fungus: 80 represented nearly complete inhibition but some growth of the fungus; 50 represented partial inhibition of growth or early complete inhibition with later growth: 20 indicated some, but not significant, inhibition of growth; and 0 indicated complete growth of the fungus without any inhibition.

As in the case of the seven fungus species discussed above, the results representing the effectiveness of the compounds of Table I against *Cercospora arachidicola* are included in Table II under the title "CER 500."

TABLE II

| Cpd. No. | ALT 500 Ex. 18 | BBL 1000 Ex. 17 | BMP 1000 Ex. 13 | BMS 250 Ex. 12 | BOT 500 Ex. 18 | BRE 1000 Ex. 15 | CER 500 Ex. 18 | CMS 250 Ex. 12 | FUS 500 Ex. 18 | HMAY 500 Ex. 18 | PHY 500 Ex. 18 | PMP 1000 Ex. 18 | PNT 900 Ex. 16 | RCB 1000 Ex. 14 | SCM 500 Ex. 18 | SCO 500 Ex. 18 |
|---|---|---|---|---|---|---|---|---|---|---|---|---|---|---|---|---|
| 1 | 50 | 0 | 60 | 90 | 100 | 100 | 100 | 90 | 0 | 100 | 100 | 90 | — | 100 | 0 | 100 |
| 2 | 95 | 0 | 100 | 100 | 100 | 0 | 100 | 65 | 90 | 100 | 70 | 85 | 82 | 0 | 0 | 65 |
| 3 | 100 | 0 | 100 | 100 | 100 | 90 | 100 | 90 | 70 | 100 | 0 | 100 | 82 | 60 | 0 | 10 |
| 4 | 90 | 15 | 100 | 100 | 90 | — | 100 | 90 | 90 | 100 | 100 | — | 55 | 0 | 0 | 50 |
| 5 | 100 | 0 | 100 | 100 | 100 | — | 100 | 90 | 90 | 100 | 100 | 90 | 82 | 0 | 0 | 100 |
| 6 | 95 | 15 | 90 | 100 | 100 | 95 | 100 | 90 | 80 | 100 | 100 | 80 | 82 | 20 | 45 | 35 |
| 7 | 100 | 0 | 100 | 100 | 100 | 100 | 100 | 80 | 40 | 100 | 100 | 100 | 95 | 100 | 25 | 10 |
| 8 | 100 | — | 100 | 100 | 100 | 100 | 100 | 90 | 95 | 100 | 100 | 65 | — | 85 | 0 | 100 |
| 9 | 50 | 0 | 90 | 90 | 60 | 100 | 100 | 0 | 0 | 100 | 65 | 100 | 0 | 0 | 0 | 0 |
| 10 | 75 | 0 | 15 | 0 | 100 | 100 | 100 | 80 | 50 | 100 | 40 | 100 | 0 | 0 | 0 | 0 |
| 11 | 95 | — | 15 | 60 | 50 | 100 | 100 | 60 | 50 | 90 | 0 | 0 | — | 0 | 0 | 0 |
| 12 | 80 | — | 0 | 60 | 0 | 0 | 100 | 60 | 50 | 80 | 0 | 0 | — | 0 | 5 | 55 |
| 13 | 35 | — | 0 | 45 | 100 | 0 | — | 0 | 25 | 70 | 35 | 0 | — | 0 | 0 | 0 |
| 14 | 60 | — | 0 | 0 | 95 | 0 | 0 | 90 | 20 | 75 | 30 | 0 | — | 0 | 15 | 45 |
| 15 | 65 | — | 0 | 70 | 90 | 0 | 0 | 95 | 25 | 35 | 20 | 0 | — | 0 | 5 | 0 |
| 16 | 70 | — | 0 | 15 | 100 | 0 | 0 | 100 | 30 | 20 | 10 | 0 | — | 0 | 0 | 45 |
| 17 | 60 | — | 0 | 0 | 95 | 0 | — | 50 | 30 | 70 | 0 | 0 | — | 0 | 0 | 0 |
| 18 | 60 | — | 65 | 0 | 100 | 0 | — | 0 | 30 | 80 | 85 | 0 | — | 0 | 0 | 45 |
| 19 | 75 | — | 15 | 0 | 100 | 0 | — | 0 | 30 | 55 | 65 | 0 | — | 0 | 0 | 100 |
| 20 | 60 | — | 0 | 0 | 100 | 0 | 100 | 25 | 10 | 65 | 10 | 0 | — | 0 | 40 | 0 |
| 21 | 70 | — | 0 | 0 | 75 | 0 | 0 | 50 | 20 | 45 | 0 | 0 | — | 0 | 0 | 0 |
| 22 | 0 | — | 50 | 40 | 25 | 0 | 100 | 100 | 10 | 15 | 10 | 0 | — | 0 | 0 | 20 |
| 23 | 0 | — | 85 | 0 | 0 | 0 | 0 | 0 | 0 | 70 | 0 | 95 | — | 35 | 0 | 40 |
| 24 | 10 | — | 0 | 0 | 0 | 0 | 100 | 40 | 25 | 30 | 15 | 0 | — | 0 | 0 | 85 |
| 25 | 0 | — | 0 | 0 | 0 | 0 | 0 | 20 | 0 | 30 | 0 | 0 | — | 15 | 0 | 75 |
| 26 | 0 | — | 0 | 0 | 0 | 0 | 100 | 0 | 0 | 20 | 0 | 0 | — | 0 | 0 | 50 |
| 27 | 100 | — | 0 | 75 | 100 | 100 | 0 | 90 | 10 | 100 | 80 | 0 | — | 0 | 0 | 100 |
| 28 | 20 | — | 25 | 50 | 100 | 0 | 100 | 50 | 75 | 50 | 0 | 0 | — | 0 | 0 | 85 |
| 29 | 40 | — | 25 | 90 | 75 | 0 | 100 | 50 | 10 | 70 | 5 | 95 | — | 0 | 0 | 100 |
| 30 | 40 | — | 100 | 50 | 100 | 0 | 100 | 50 | 10 | 70 | 10 | 0 | — | 0 | 25 | 40 |
| 31 | 20 | — | 80 | 0 | 85 | 100 | 100 | 0 | 5 | 75 | 0 | 0 | — | 0 | 0 | 100 |
| 32 | 40 | — | — | 15 | 85 | 0 | 100 | 0 | 15 | 75 | 5 | 95 | — | 0 | 0 | 70 |
| 33 | 100 | — | 0 | 65 | 90 | 0 | 100 | 40 | 20 | 65 | 15 | 0 | — | 0 | 0 | 0 |
| 34 | 70 | — | 0 | 100 | 100 | 100 | 100 | 0 | 75 | 65 | 0 | 95 | — | 0 | 0 | 25 |
| 35 | 90 | — | 0 | 90 | 100 | 100 | 100 | 15 | 70 | 70 | 5 | 50 | — | — | 0 | 100 |
| 36 | 100 | — | 0 | 100 | 100 | 100 | 100 | 65 | 100 | 30 | 10 | 100 | — | 0 | 0 | 0 |
| 37 | 100 | — | — | 85 | 100 | 100 | 100 | 15 | 100 | 100 | 5 | 95 | — | 0 | 0 | 50 |
| 38 | 100 | — | 100 | 100 | 75 | 100 | 100 | 0 | 100 | 50 | 0 | 70 | — | — | 0 | 25 |
| 39 | 100 | — | 100 | 100 | 100 | 100 | 100 | 35 | 100 | 70 | 0 | 95 | — | 0 | 0 | 25 |
| 40 | 100 | — | 100 | 100 | 100 | 100 | 100 | 35 | 100 | 100 | 0 | 0 | — | 0 | 0 | 25 |
| 41 | — | — | — | — | — | — | — | — | — | — | — | — | — | — | — | — |
| 42 | 0 | — | 0 | 15 | 30 | 0 | 100 | 20 | 15 | 35 | 0 | 0 | — | 0 | 0 | 0 |
| 43 | 0 | — | 0 | 15 | 0 | 0 | 0 | 20 | 0 | 20 | 0 | 0 | — | 0 | 0 | 0 |
| 44 | 70 | — | — | 35 | 100 | 100 | 100 | 40 | 60 | 65 | 0 | 100 | — | — | 0 | 100 |
| 45 | 60 | — | — | 85 | 0 | 95 | 100 | 90 | 85 | 75 | 0 | 90 | — | — | 0 | 40 |
| 46 | — | — | — | — | — | — | — | — | — | — | — | — | — | — | — | — |
| 47 | 70 | — | — | 85 | 65 | 100 | 100 | 90 | 95 | 65 | 0 | 95 | — | — | 0 | 40 |
| 48 | 60 | — | — | 90 | 100 | 100 | 100 | 100 | 100 | 75 | 0 | 95 | — | — | 0 | 0 |
| 49 | 60 | — | — | 15 | 80 | 90 | 0 | 0 | 50 | 55 | 0 | 0 | — | — | 0 | 0 |

The above embodiments and examples are given to illustrate the scope and spirit of the instant invention. These embodiments will make apparent, to those skilled in the art, other embodiments and examples. These other embodiments and examples are within the contemplation of the present invention. Therefore, this invention should be limited only by the appended claims.

What is claimed is:

1. A compound having the structural formula

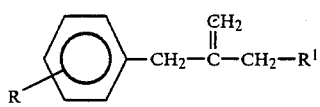

where R is $C_1$-$C_8$ alkyl, $C_3$-$C_6$ cycloalkyl, trifluoromethyl, phenyl, phenoxy, or benzyl and $R^1$ is an at least partially saturated pyridyl which is attached to the 2-propenyl moiety through the nitrogen atom, and which may be substituted with lower alkyl, or a physiologically acceptable salt thereof.

2. A compound in accordance with claim 1 where R is $C_1$-$C_6$ alkyl, $C_5$-$C_6$ cycloalkyl, trifluoromethyl, phenyl, phenoxy or benzyl; and $R^1$ is optionally substituted with $C_1$-$C_2$ alkyl.

3. A compound in accordance with claim 2 wherein R is t-butyl, cyclohexyl, trifluoromethyl, phenyl or phenoxy; and $R^1$ is optionally substituted with one or two methyl substituents.

4. A compound in accordance with claim 3 wherein R is positioned para to the substituted propenyl group.

5. A composition comprising the compound of claim 1 and a suitable carrier therefor.

6. A method for controlling phytopathogenic fungi comprising applying a fungicidally effective amount of the compound of claim 1 to the locus under attack by said fungi.

7. A method for controlling phytopathogenic fungi comprising applying a fungicidally effective amount of the compound of claim 1 to the foliage of the plant to be protected from said fungi.

8. A method in accordance with claim 7 wherein said compound is applied to said foliage in the concentration in the range of between about 10 and about 500 milligrams per liter.

9. A method for controlling phytopathogenic fungi comprising applying a fungicidally effective amount of the compound of claim 1 to the soil in which the plant to be protected from phytopathogenic fungi is grown.

10. A method in accordance with claim 9 wherein said compound is applied to the soil in a concentration in the range of between about 0.125 and about 10 kilograms per hectare.

11. A method for controlling phytopathogenic fungi comprising coating seeds of the plant to be protected with a fungicidally effective amount of the compound of claim 1.

12. A method in accordance with claim 11 wherein said coating is applied in a concentration in the range of between about 5 and about 75 grams of compound per 100 kilograms of seed.

* * * * *